(12) United States Patent
Whitman et al.

(10) Patent No.: US 6,368,286 B1
(45) Date of Patent: Apr. 9, 2002

(54) PNEUMOTHORAX DETECTOR

(76) Inventors: Eric D. Whitman, 38 Aberdeen Pl., St. Louis, MO (US) 63105; Steven R. Frank, 11192 Twin Spruce Rd., Jefferson, CO (US) 80403

( * ) Notice: Subject to any disclaimer, the term of this patent is extended or adjusted under 35 U.S.C. 154(b) by 0 days.

(21) Appl. No.: 09/322,850

(22) Filed: May 28, 1999

Related U.S. Application Data

(60) Provisional application No. 60/087,985, filed on Jun. 4, 1998.

(51) Int. Cl.$^7$ ................................................. A61B 5/08
(52) U.S. Cl. ....................................................... 600/529
(58) Field of Search ................................. 600/529, 534, 600/538, 586, 552, 407, 431, 436

(56) References Cited

U.S. PATENT DOCUMENTS 6,168,568 B1 * 1/2001 Gavriely ..................... 600/529

* cited by examiner

*Primary Examiner*—George Manuel
(74) *Attorney, Agent, or Firm*—Paul M Denk

(57) ABSTRACT

Method and device for detecting life-threatening pneumothorax caused by air in the thoracic or chest cavity by passive auditory detection using an array of transducers placed on the patient's chest and operatively connected to a data processing unit. The unit is programmed to filter out sounds not in the harmonic of the bubbling air associated with a pneumothorax. In addition to passive auditory detection ultrasound techniques and radio active gas detection, are shown to be used.

16 Claims, 6 Drawing Sheets

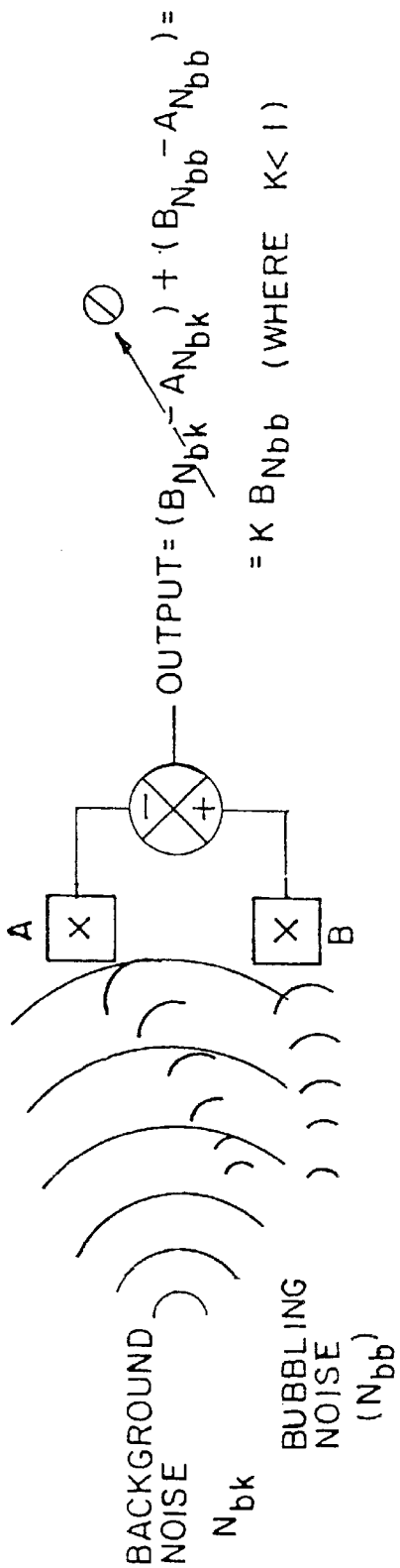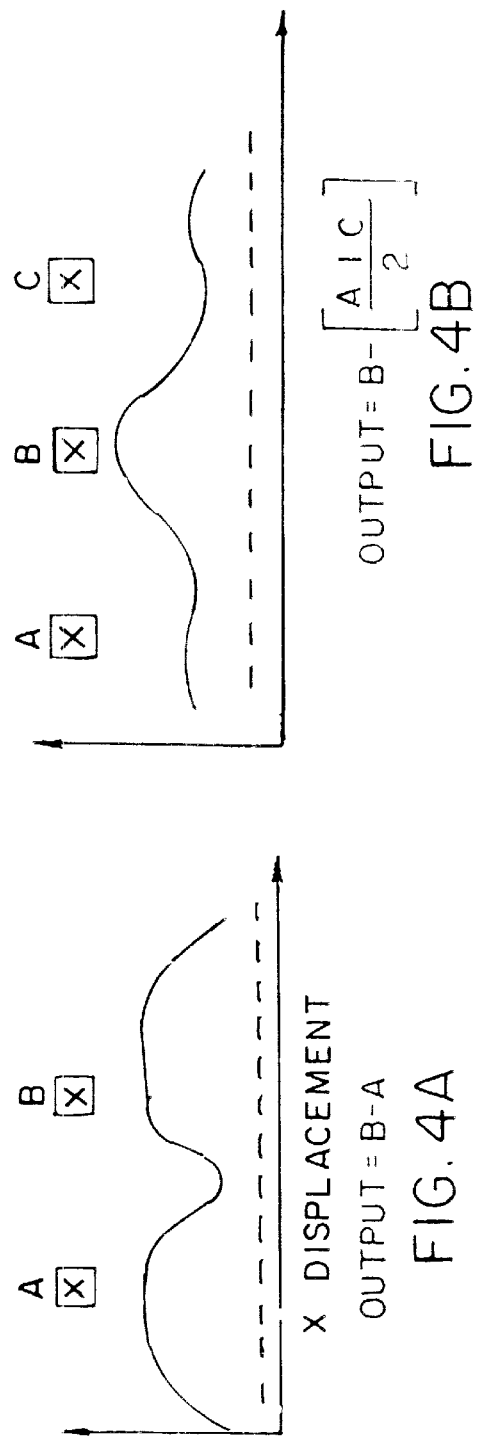
FIG. 4
FIG. 4A
FIG. 4B

PNEUMOTHORAX DETECTOR

CROSS-REFERENCE TO RELATED APPLICATIONS

This application claims priority to provisional application Ser. No. 60/087,985, filed Jun. 4, 1998.

BACKGROUND OF THE INVENTION

Pneumothorax is a life-threatening condition that occurs when the lung outer membrane is injured by a sharp object and air leaks into the thoracic or chest cavity. The air can then build up inside the chest cavity, compress the heart and lungs and deprive the victim of oxygen. The condition also may cause a drop in blood pressure and, in severe cases, result in sudden death from acute heart failure, Pneumothoraces are observed clinically as a result of many conditions, principally as the result of trauma (i.e. car accidents with rib fractures, stab wounds, and bullet wounds). Pneumothorax can be a complication of central venous catheter (CVC) insertion surgical procedures for intravenous access.

The clinician generally obtains a standard chest radiograph picture when a pneumothorax is suspected clinically. Or, in the case of catheter insertions, X-rays are obtained to prove postoperatively that pneumothorax has not occurred. The radiograph is costly, can be delayed due to personnel or equipment unavailability, and exposes the patient and surrounding healthcare personnel to potentially harmful ionizing radiation. To date, no other method has been described that enables the non-invasive diagnosis or exclusion of pneumothorax without some form of ionizing radiation imaging.

It would be advantageous, therefore, to provide a device to determine if a pneumothorax exists which eliminates the need for chest radiographs in the overwhelming majority of cases. It would also be advantageous if the device can be used to detect heart valve abnormalities, bone and joint problems, and blood vessel flow disturbances.

SUMMARY OF THE INVENTION

It is among the several objects of the present invention to provide a device that can detect the presence of pneumothorax without the use of ionizing radiation, or any invasive procedure such as a needle puncture of the skin.

It is another object of the present invention to provide a device that can detect the presence of pneumothorax using ultrasonic techniques.

Another object of the present invention to provide a device that can detect the presence of pneumothorax using passive auditory detection.

Yet another object of the present invention to provide a device that can detect the presence of pneumothorax using mildly radioactive ideal gas.

Yet another object of the present invention to provide a device that can detect the presence of pneumothorax that is portable and easy to use.

In accordance with invention, generally stated, the preferred embodiment includes a passive auditory detection system having an array of listening device (transducers) which can be moved freely over the patient's body surface. This array returns its signal to the central processing unit which filters, band-shifts and conditions the signal to reject ambient noise and focus on the area of interest. This conditioned signal is then presented to the user auditorily.

In another embodiment, a portable device for detecting a pneumothorax, comprising an ultrasonic probe for coupling the pulse to the chest and receiving the echo. The probe delivers its signal to the central processing unit. The central processing unit performs the correlations, normalizations and then presents the information visually and auditorily to the user.

Another embodiment includes a dispenser/mixer to allow inspiration of a mixture of the mildly radioactive gas and air. The detection device consists of a radiation detecting device such as a scintillation crystal and photomultiplier tube or a Geiger-Mueller tube or a solid-state detector. This detector is coupled to a signal conditioning and presentation system which provides a visual and auditory indication of the received signal strength.

All of three of the embodiments of the device can include an on-board microprocessor or digital signal processor for interpretation of the information, to provide clinically relevant information to the user, and eliminate the need for the user to be able to personally interpret the signals. This interpretation could provide the user with a "yes/no" indication of a specific condition, or alternatively, could determine that further testing (i.e., a chest radiograph) was necessary to evaluate for this condition

BRIEF DESCRIPTION OF THE DRAWINGS

FIG. 4 is an algorithmic illustration of the cancellation of background noise used with the system of FIG. 3;

FIG. 4A is a graphic depiction of background noise cancellation;

FIG. 4B is another graphic depiction of background noise cancellation;

Corresponding reference numbers indicate corresponding elements throughout the various illustrations.

DESCRIPTION OF THE PREFERRED EMBODIMENT

Figure 1:
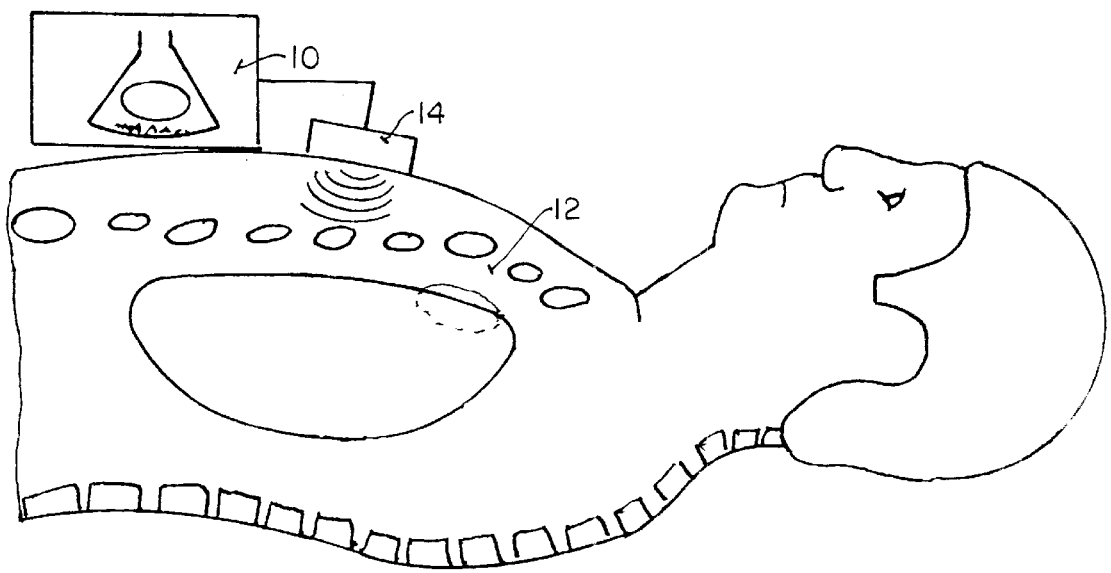
FIG. 1 is side view of one embodiment of an ultrasonic pneuomothorax detector applied to a patient, the thoracic cavity of patient shown in cross-section.
Figure 1A:
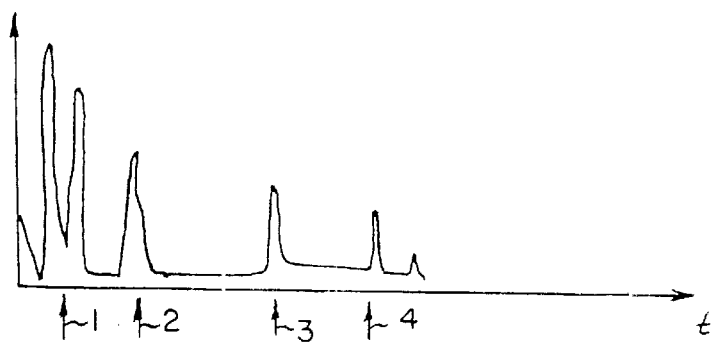
FIG. 1A is a graphic depiction of a normal ultrasonic scan of a patient's thoracic cavity obtained by the device of FIG. 1.
Figure 8:
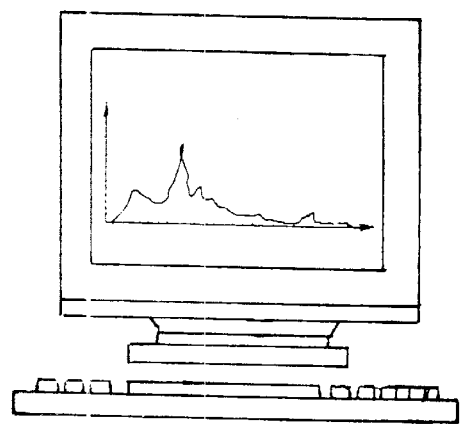
FIG. 8 is a front view of a display monitor employed in the present invention.

Ultrasound:

One embodiment of the device utilizes ultrasound and is illustrated generally in FIG. 1. The ultrasound technique is used to detect an unnatural pocket of air in the thoracic cavity. A low-frequency ultrasound unit 10 is coupled into the patient's chest cavity 12 by a probe 14. Probe 14 is designed to detect air through bone. The key component of the probe is the circuitry that processes the signal. The reflection from the chest is analyzed and presented to the user either auditorily or visually. For example, a display unit as shown in FIG. 8 can be adapted for display of the ultrasound results. When the ultrasound reflects from the density boundaries internal to the body, the strength of the reflection in association with the time that the reflection is received will allow the system/user to determine the nature of the boundary. The strongest reflections occur at boundaries of fluid and air such as would be experienced when a pneumothorax is encountered by the sound beam. The next strongest would occur at the boundary with bone. See FIG. 2.

Due to the boundary with bone always occurring between the region of surface contact and the region of interest, the gain applied to the reflected signal would be compensated to normalize the loss as the reflections behind this region would have to transgress it twice. Compensation in this will increase the sensitivity of the system to the nature of the tissue and interfaces behind the bone. The system will always be able to do this automatically as it will get a very strong and clear indication of when the bone is between the area of contact and the intended area of interest.

Since the bone will be encountered before the area of interest, the time component of when the signal is received can be used to "blank" the output to the user to exclude this information. This will allow only the information from behind the bone to be presented for evaluation. Time filtering the return echo in this way will dramatically simplify the user interpretation of the tissue behind the bone for the air/fluid boundary.

Passive Auditory Detection

A preferred embodiment of the present invention can be referred to generally as the passive auditory detection device. In the event of pneumothorax, the leak will generate a pocket of gas by leaking air to the space between the lung and its surrounding tissue environment. This leaking of air has a characteristic sound with a distinct harmonic as it bubbles through the interstitial fluids and space. The preferred embodiment is specifically designed to detect this sound.

Figure 2:
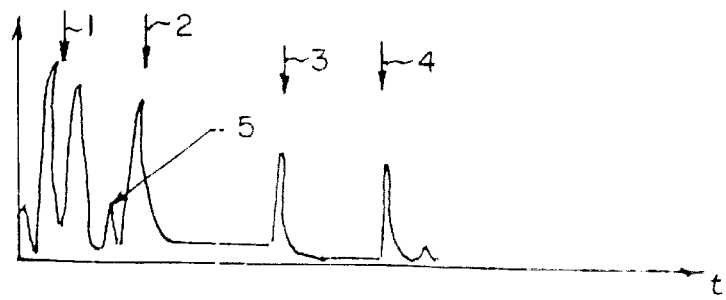
FIG. 2 is a graphic depiction of an abnormal ultrasonic scan of a patient'thoracic cavity obtained by the device of FIG. 1.
Figure 3:
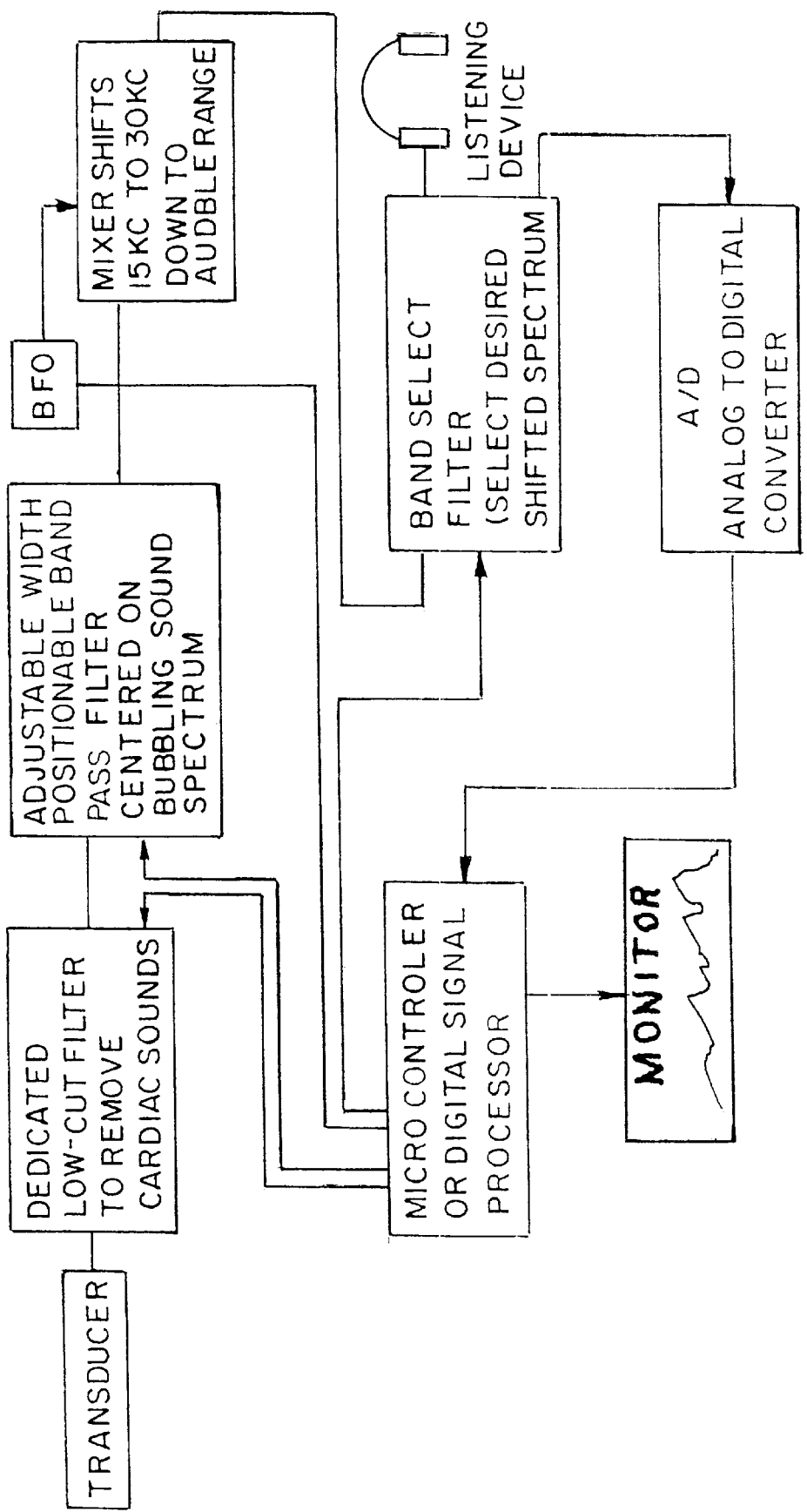
FIG. 3 is a schematic flow diagram illustrating a passive auditory pneumothorax detection system of the present invention.
Figure 9:
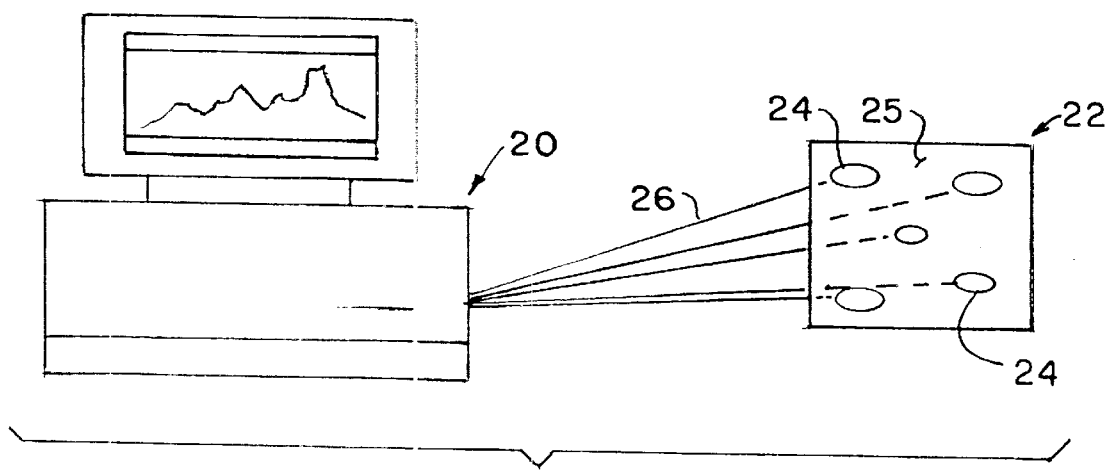
FIG. 9 is an illustration of the passive auditory detection system of the present invention.

There are two main components of the passive auditory detection device, a non-disposable hardware or central processing unit, indicated generally as numeral 20 in FIG. 9 that is used to interpret and process signals and the disposable transducer component 22, that is attached to the patient. Central processing unit 20, that can include generic digital signal processing chips, can be a conventional PC, as shown, or a handheld device (not shown). The novel transducer 22 of the present invention includes a series of two (2) to five (5) or more transducers 24 on a self-adhesive patch 25 and wired in parallel, for example with wires 26 to the central processor 20. The patch 25 with transducers 24 is adhered to the patient's chest. Signals from the individual transducers 24 are combined algebraically as shown in FIG. 2 to attenuate artifact noise such as room noise and patient movement. The array of transducers 24 allows for the localization of the pneumothorax within the chest cavity as will be explained below.

The central processing unit 20 includes software, which is written to perform the functions graphically illustrated in FIGS. 1A through 4B. The basic function of the software is to receive a digital sound signal received from transducers 24 in such a way as to detect the presence of a pneumothorax. The software processes a digital sound signal by filtering out frequencies far away from a set point, which is the frequency of air bubbling out of the lung. The transducers 24 algebraically eliminate motion artifact and room noise, as shown in FIG. 4. The software also shifts the frequencies to maximize the auditory detection of the pneumothorax. The software is written to analyze the resultant sound pattern and decide the likelihood of pneumothorax based upon probabilities. The software uses data obtained during product development using either a neural network, genetic algorithms, or rule-based decision making.

Figure 7:
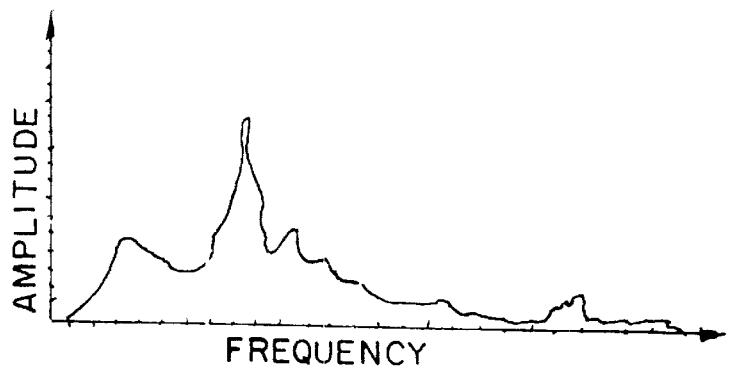
FIG. 7 is a frequency domain representation of an audio signal produced by one embodiment of the present invention.

For gross location of a suspected area, a filtered electronic listening device will be used which couples high-sensitivity listening device to the exterior of the body (ex. Transducers 24). This device is tuned to reject frequencies above and below the most prominent harmonic of the bubbling sound, as stated above. It also uses two or more transducers configured only a small distance apart. The signals from these transducers will be combined algebraically (as shown in FIG. 4) to greatly attenuate the room noise and patient movement artifacts. The bubbling noise will be maximum when it is closer to one of the transducers than the other(s). In this way, the array of transducers can be "focused" to an area of interest and greatly reject the extraneous noises of the room and the movement over the chest cavity. Additionally, the filtering of the signal before presentation to the user will allow large low-frequency sounds such as the heart to be attenuated allowing the gain for the audio spectrum of interest to be increased. This will produce a listening device which is far superior to the conventional stethoscope that is currently available. For example, a frequency domain audio signal provided to the uses is illustrated in FIG. 7.

Once an area of suspected pneumothorax is detected, the mode of the listening device can be switched to the spectral shift mode. In this mode, the sound received in the ranges which are not well transmitted through a normal stethoscope are shifted into the prime audio range (1 kc to 5 kc). The range select allows shifting of sound that would normally fall beyond the range of most human hearing (>15 kc) into the range of peak human hearing (1 kc to 5 kc). (See FIG. 3). This is done in a simple mixer circuit utilizing a variable beat frequency oscillator (BFO) mixer and filter arrangement to shift and select the desired range of frequencies. This should allow the user to quite clearly hear and recognize the bubbling sound associated with the pneumothorax.

The listening device can be set into any number of pre-arranged filtering or spectrum shifting configurations to optimize the information gathered for diagnosing many internal problems. For instance, it could be optimized to listen to the heart or to listen to the valves of the heart. It could be optimized to listen to the joints to diagnose ligament or cartilage problems. It could filter out other sounds, enhancing the effectiveness of Doppler flow analyses for vascular or blood vessel abnormalities. These preselected optimized configurations would augment the capability to manually select a pass-band and a spectrum shift. The manual operation allows the sophisticated user the ability to get the most out of the listening device.

A display monitor, as shown in FIG. 8, can be used to allow the user to visually monitor a patient and would provide information in addition to the information derived from the described passive listening embodiment. This information may include a visual output corresponding to the patient's breathing pattern, graphically showing any abnormalities that may be from a pneumothorax.

Figure 5:
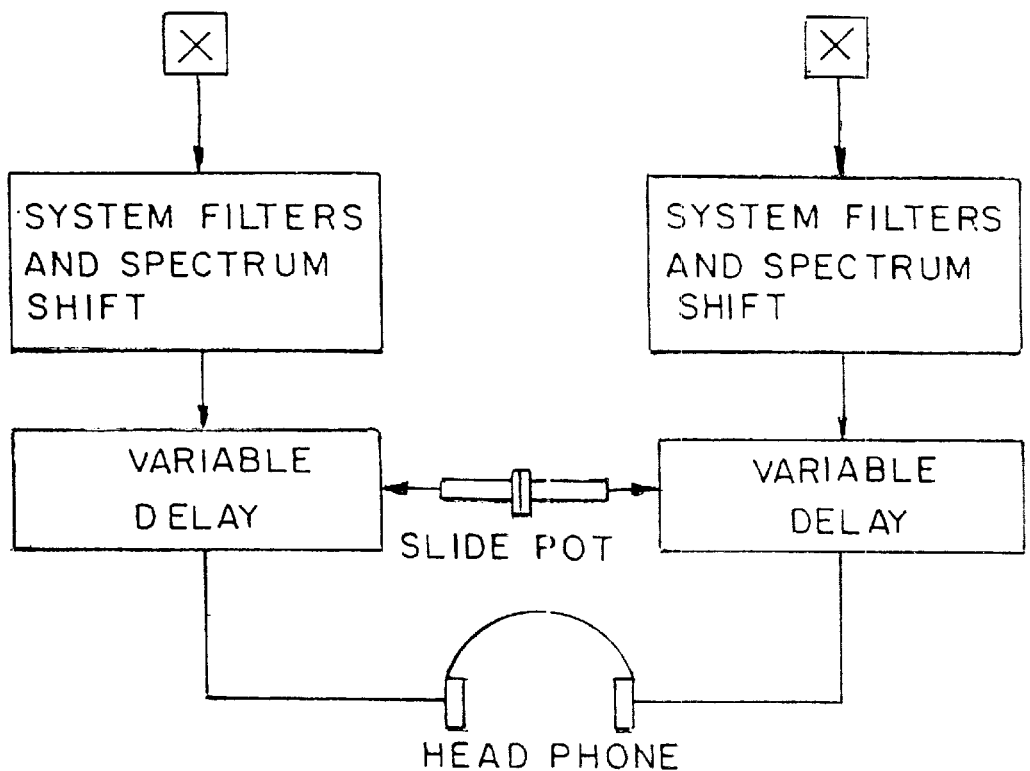
FIG. 5 is a schematic flow diagram illustrating focused stereo scanning of the system illustrated in FIG. 3.
Figure 5A:
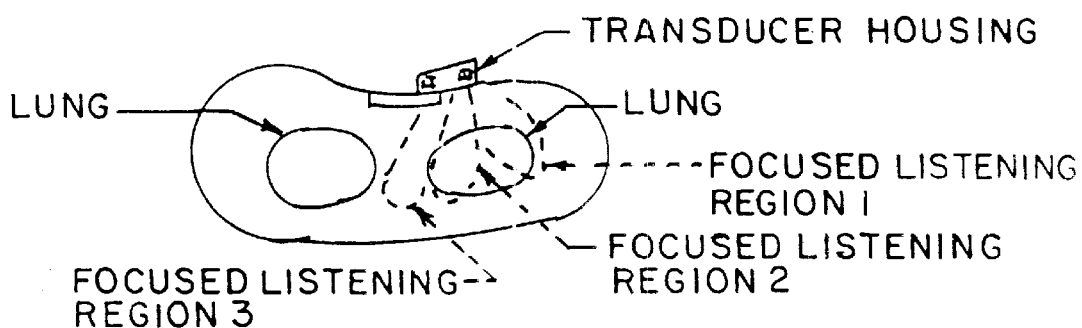
FIG. 5A is transectional view of a thoracic cavity illustrating the application of focused stereo scanning of FIG. 5.

Additionally, the information retrieved from the multi-sensor array can be simply processed to provide stereo image presentation allowing the user to perceive directionality and depth. (See FIGS. 5 and 8). This would be particularly useful to diagnose knee, hip, shoulder, or elbow joint pain and dysfunction. The device can accommodate numerous transducer arrays and thus allows positioning of the arrays on either side of the area of interest. An example of this could be anterior and posterior placements.

In summary, this device will allow the user to hear, locate and characterize sounds within the body that were previously in-audible or too heavily masked by other sounds as to be useful.

Radioactive Gas Detection

The third embodiment of the invention utilizes a mildly radioactive ideal gas such as Xenon. The patient inspires a quantity of the gas mixed with air and then holds their breath. The patient then "bares down" abdominally to increase the pressure in the chest cavity. This will force some of the radioactive gas through any existing pneumothorax and into the pocket of gas which is being created. The patient then expires normally.

Figure 6:
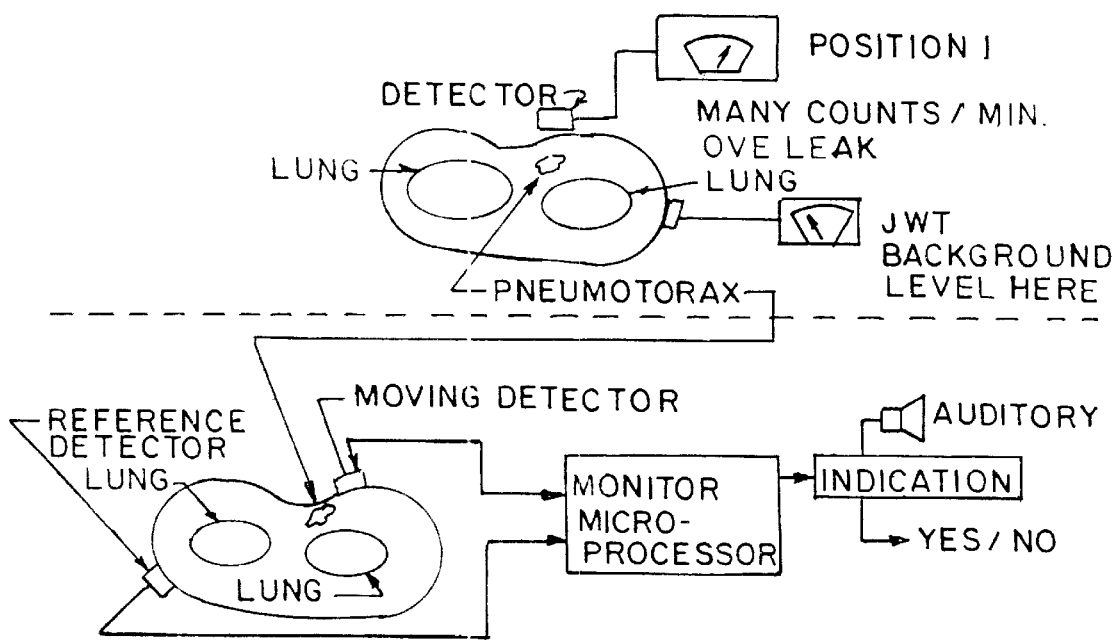
FIG. 6 is a flow diagram illustrating the radioactive gas pneumothorax detection system of the present invention.

After a couple of normal breaths, a device which consists of a simple radiation detector, is passed over the patient's chest. A low level of background radiation will be detected as some of the Xenon has been retained in the lung and some has been distributed systemically through the blood. (See FIG. 6). In the event that a pneumothorax exists, a pocket of radiation greater than the background level will be easily identifiable with the radiation detecting probe.

Signal Processing and Clinical Interpretation/Recommendations.

In general, and with all illustrated embodiments, processed signals will be analyzed by on-board microprocessor (s) and/or digital signal processor(s), to provide clinically relevant information for patient care. These interpretations might provide the user with a "yes/no" indication of a specific condition, or alternatively, could determine that further testing was necessary to evaluate for this condition (see FIG. 1). For example, the invention might determine that chest signals were uninterpretable or inadequate for interpretation, and that a chest radiograph was necessary to determine if a pneumothorax was present. In another embodiment, the invention might communicate the probability of the presence of a pneumothorax due to the processed signal content, and advise that a chest radiograph was necessary, for instance, if the probability rose above the fiftieth percentile. In orthopedic applications, signal characteristics and/or location might point to a specific bony or soft tissue injury, such as a tear (full or partial) of the medial collateral ligament of the knee. The invention will include a visual display designed to clearly convey these interpretations to the user (see FIG. 3).

Variations or modifications to the subject matter of this invention, and the structure and usefulness of the pneumothorax detector of this invention, may occur to those skilled in the art upon reviewing the disclosure herein. Such variations or modifications, if within the spirit of this invention, are intended to be encompassed within the scope of the invention as described. The description of the preferred embodiment, as shown and analyzed herein, is done so for illustrative purposes only.

What is claimed is:

1. A method of detecting the presence of abnormal air in the thoracic cavity of a patient comprising:

attaching an array of transducers to the chest of the patient, the transducers being tuned to reject frequencies above and below the most prominent harmonic of the sound of air bubbling though interstitial fluids and space, the transducers forming signals indicative of the sound emanating from the chest of the patient;

transmitting the transducer signal to a central processing unit;

eliminating from the transducer signal any artifact noise, resulting in presentation only of sounds emitted by abnormal air in the thoracic cavity.

2. The method of claim 1 wherein the array of transducers includes at least two transducers.

3. The method of claim 1 wherein the array of transducers is attached to a patch.

4. The method of claim 1 wherein the central processing unit is programmed to algebraically eliminate artifact noise.

5. A method of detecting a pneumothorax in the chest of a patient with a suspected pneumothorax comprising:

applying a high sensitivity listening device comprised of at least two transducers to the chest of the patient; said at least two transducers generating a transducer signal indicative of sounds emanating from the chest of the patient;

transmitting the transducer signal to a central processor, said central processor being programmed to reject sound frequencies above and below a prominent harmonic for sound produced by a pneumothorax to produce a resulting signal; and examining the resulting signal to determine the presence of a pneumothorax.

6. A method of detecting the presence of a pneumothorax in the chest cavity of a patient comprising:

having the patient inspire mildly radioactive gas:

applying a radiation detector to the patient's chest;

detecting an elevated concentration of the mildly radioactive so as to determine the presence of a pneumothorax in the chest cavity.

7. The method of claim 6 wherein the mildly radioactive gas is xenon.

8. A device for detecting the presence of pneumothorax in the chest cavity of a patient comprising:

a central processing unit; and an array of transducers operatively connected to said central processor, said array of transducers capable of detecting and transmitting sounds emanating from within the chest cavity of the patient to said central processing unit;

said central processing unit programmed to filter out sounds emanating from the chest cavity which are above and below the normal harmonic of sounds produced by the presence of a pneumothorax in the chest cavity of a patient thereby leaving for detection only those sounds within the normal harmonic of sounds produced by a pneumothorax in the chest cavity of a patient.

9. The device of claim 8 further including at least one speaker.

10. The device of claim 8 further comprising a monitor.

11. The device of claim 8 where in said array of transducers further comprises at least two individual transducers within the array.

12. The device of claim 11 wherein the individual transducers are secured to an adhesive patch.

13. The device of claim 8 wherein the array of transducers is operatively connected to the central processor in parallel.

14. A method of detecting the presence of abnormal air in the thoracic cavity of a patient comprising:

attaching a probe to the chest of the patient;

transmitting sound into the patient's chest using the probe;

receiving reflected sound signals at the probe;

eliminating from the transmitted sound any artifact noise resulting in a presentation only of sounds emitted by abnormal air in the thoracic cavity.

15. The method of claim 14 wherein the probe is part of a low-frequency ultrasound unit.

16. The method of claim 14 wherein the central processing unit is programmed to algebraically eliminate artifact noise.

* * * * *